United States Patent
Owen et al.

(10) Patent No.: US 9,289,187 B2
(45) Date of Patent: Mar. 22, 2016

(54) IMAGING TRANSDUCER PROBE

(75) Inventors: Robert H. Owen, Stenløse (DK);
Henrik Jensen, Bagsværd (DK)

(73) Assignee: B-K Medical Aps, Herlev (DK)

( * ) Notice: Subject to any disclaimer, the term of this patent is extended or adjusted under 35 U.S.C. 154(b) by 145 days.

(21) Appl. No.: 13/992,878

(22) PCT Filed: Dec. 10, 2010

(86) PCT No.: PCT/IB2010/003198
§ 371 (c)(1),
(2), (4) Date: Jun. 10, 2013

(87) PCT Pub. No.: WO2012/076918
PCT Pub. Date: Jun. 14, 2012

(65) Prior Publication Data
US 2013/0261466 A1    Oct. 3, 2013

(51) Int. Cl.
*A61B 8/14*    (2006.01)
*A61B 8/00*    (2006.01)
(Continued)

(52) U.S. Cl.
CPC ............... *A61B 8/4461* (2013.01); *A61B 8/12* (2013.01); *A61B 8/4455* (2013.01); *A61B 8/4488* (2013.01); *A61B 8/4254* (2013.01); *A61B 8/445* (2013.01); *A61B 8/467* (2013.01); *A61B 8/483* (2013.01); *A61B 8/56* (2013.01)

(58) Field of Classification Search
USPC .............................. 600/407, 437–472; 439/11
See application file for complete search history.

(56) References Cited

U.S. PATENT DOCUMENTS

| 3,964,296 A | 6/1976 | Matzuk |
| 5,070,879 A | 12/1991 | Herres |

(Continued)

FOREIGN PATENT DOCUMENTS

| JP | S56-1981-156141 | 12/1981 |
| JP | H01991-182237 | 8/1991 |
| JP | 2004-141428 | 5/2004 |

OTHER PUBLICATIONS

Jacek F. Gieras. "Electric Motors for Medical and Clinical Applications." Advancements in Electric Machines, Power Systems 2008, pp. 135-156 (25 pages total, including date, author and publication information).*

(Continued)

*Primary Examiner* — James Kish
(74) *Attorney, Agent, or Firm* — Driggs, Hogg, Daugherty & Del Zoppo, Co. LPA; Anthony M. De Zoppo, III (57) ABSTRACT

An ultrasound imaging probe includes a housing (202) having a long axis and an elongate tubular shaft (214) including an internal cavity and first and second end portions (218, 220). The shaft extends along the long axis and is rotatably supported in the housing for rotation relative to the housing through an angular range including one hundred and eighty degrees to a predetermined maximum angle. The probe further includes a transducer array (222), including a plurality of transducer elements along the long axis, affixed to the first end portion (218) of the shaft. The probe further includes an electrical connector (228) fixedly mounted in the housing. The probe further includes an physical electrical pathway (226) having first and second ends and extending along and in the internal cavity of the shaft, wherein a first end of the pathway is connected to transducer array and a second end of the pathway is connected to the electrical connector.

23 Claims, 5 Drawing Sheets

(51) Int. Cl.
*A61B 8/12* (2006.01)
*A61B 8/08* (2006.01)

(56) References Cited

U.S. PATENT DOCUMENTS

| | | |
|---|---|---|
| 5,152,294 A | 10/1992 | Mochizuki et al. |
| 5,159,931 A | 11/1992 | Pini |
| 5,460,179 A | 10/1995 | Okunuki et al. |
| 5,762,066 A * | 6/1998 | Law et al. .................. 600/439 |
| 5,782,769 A | 7/1998 | Hwang et al. |
| 6,203,498 B1 | 3/2001 | Bunce et al. |
| 6,213,948 B1 | 4/2001 | Barthe et al. |
| 6,264,607 B1 | 7/2001 | Goll et al. |
| 6,572,548 B2 | 6/2003 | Cerofolini |
| 7,081,093 B2 | 7/2006 | Flesch |
| 7,588,540 B2 | 9/2009 | Nguyen-Dinh et al. |
| 2004/0176691 A1 * | 9/2004 | Edwardsen et al. .......... 600/467 |
| 2006/0173348 A1 * | 8/2006 | Wilser et al. ................ 600/466 |
| 2007/0167821 A1 | 7/2007 | Lee et al. |
| 2010/0179431 A1 * | 7/2010 | Kosaku et al. ............... 600/462 |

OTHER PUBLICATIONS

JP2013-542614; Japanese First Office Action, dated Jul. 29, 2014.
International search report for PCT/IB2010/003198 published as WO 2012/076918 A1.

* cited by examiner

IMAGING TRANSDUCER PROBE

RELATED APPLICATION

This application is a national filing of PCT application Serial No. PCT/IB2010/003198, filed Dec. 10, 2010, published as WO 2012/076918 A1 on Jun. 14, 2012.

TECHNICAL FIELD

The following generally relates to an imaging transducer probe and finds particular application to ultrasound (US) imaging and more particularly to an US imaging probe configured to acquire data over one hundred and eighty (180) or more degrees of rotation. The following is also amenable to non-ultrasound applications.

BACKGROUND

Ultrasound (US) imaging has provided useful information about the interior characteristics of subject under examination. A general US system includes a probe with an array of transducers and a console for controlling the array of transducers for transmitting ultrasonic waves and receiving echoes, which are processed to generate images of the interior characteristics of the subject under examination, including three dimensional (3D) volumes.

Probes intended for trans-rectal and trans-vaginal use are designed for particular applications and generally include a smaller diameter elongate probe portion in which the array is affixed at or near an end region of the end of the probe portion that inserts into the rectal or vaginal cavity. Such probes have included single element and multi-element (linear and curved) arrays, and have been affixed to the end of the probe to emit signals in a direction generally parallel to the axis of the probe or emit signals in a direction generally perpendicular to the axis of the probe.

Linear array probes have been configured to pivot and/or oscillate the transducer array along a predetermined arc. By pivoting the linear array transducer to one of a plurality of predetermined angles along the arc and successively actuating the individual or groups of transducer elements at the angle, a longitudinal rectilinear scan can be performed. By oscillating the linear array transducer back and forth along the arc, and acquiring data at each of the plurality of predetermined angles a transverse scan can be performed. The rectilinear and transverse data can be used to produce echo data in orthogonal B-scan planes, creating a field of view that forms a pie-shaped cylindrical sector.

Unfortunately, the transducer array of such probes has a limited range of rotational motion, which is along the arc. As such, the probe may need to be rotated, removed and reinserted, and/or otherwise re-orientated in order to image a region of interest, which may cause discomfort to the patient and/or consumes time that could be otherwise used with the patient and/or other patients.

SUMMARY

Aspects of the application address the above matters, and others.

In one aspect, an imaging transducer includes an ultrasound imaging probe includes a housing having a long axis and an elongate tubular shaft including an internal cavity and first and second end portions. The shaft extends along the long axis and is rotatably supported in the housing for rotation relative to the housing through an angular range including one hundred and eighty degrees to a predetermined maximum angle. The probe further includes a transducer array, including a plurality of transducer elements along the long axis, affixed to the first end portion of the shaft. The probe further includes an electrical connector fixedly mounted in the housing. The probe further includes a physical electrical pathway having first and second ends and extending along and in the internal cavity of the shaft, wherein a first end of the pathway is connected to transducer array and a second end of the pathway is connected to the electrical connector.

In another aspect, a method controllably rotating a linear transducer array, of an elongate ultrasound probe inserted into a cavity of interest to image from inside the cavity, through an angle of at least one hundred and eighty degrees relative to the probe during data acquisition.

In another aspect, an ultrasound imaging system includes a console and at least one of a trans-rectal or trans-vaginal probe interfaced to the console. The console transmits a signal to the probe which causes an elongate shaft supporting a linear transducer array arrange along a long axis of the probe to rotate at least one hundred and eighty degrees during data acquisition.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
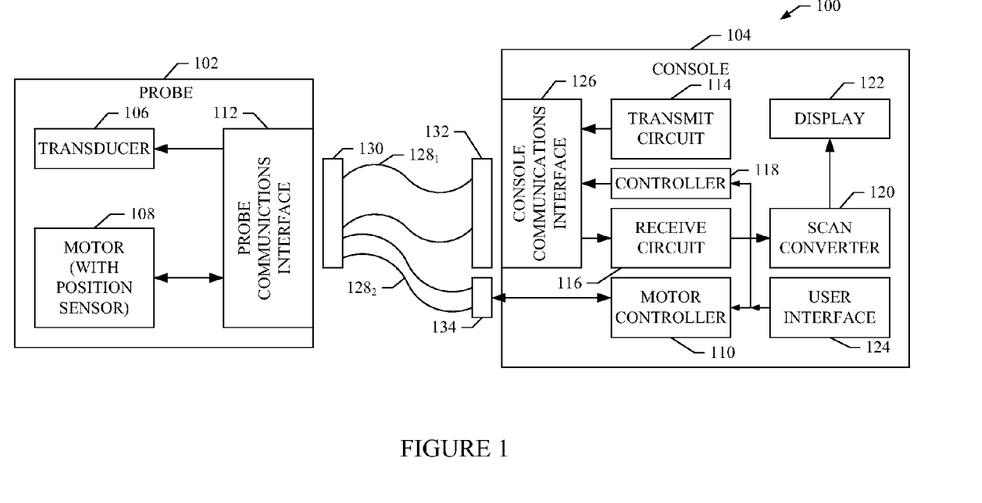
FIG. 1 illustrates an example ultrasound (US) imaging system.

FIG. 1 illustrates an imaging system 100, such as ultrasonic imaging system, including an ultrasound (US) transducer probe 102 and a console 104.

The probe 102 includes a transducer 106 with an array of transducer elements arranged along a long axis of the probe. In the illustrated embodiment, the array is a one dimensional (1D) linear array transducer 106 with one hundred and ninety-two (192) transducer elements. In other embodiments, the array 106 may have more or less transducer elements, include a two-dimensional array of elements, and/or have elements arranged in a curved or other manner.

As described in greater detail below, the transducer 106 is configured to be rotated at least one hundred and eighty degrees (180°). Examples of other suitable angles include angles up seven hundred and twenty degrees (720°), such as, for example, three hundred and sixty degrees, (360°), five hundred and sixty degrees (560°), and/or other angle of interest. Such rotation allows for high resolution, three dimensional (3D) volume data acquisitions spanning more than 180°.

A motor 108 with a position sensor is utilized to rotate the transducer array 106 and track the rotational position and rotation speed of the transducer array 106.

A probe communications interface 112 includes input and output ports for communicating data and control signals with the console 104.

The illustrated probe 102 is configured for insertion into and imaging within cavities such as the rectal, vaginal, and/or other cavity. As such, the probe 102 generally includes a protruding section, which houses the transducer elements. With trans-rectal and trans-vaginal probes, the protruding section generally has an outside diameter in a range of ten (10) to twenty five (25) millimeters (mm) such as seventeen (17) mm with a linear array of elements extending up to one hundred (100) millimeters (mm) such as sixty-five (65) mm. Probes for other applications may have smaller or larger diameters.

The console 104 includes a transmit circuit 114 that selectively actuates or excites one or more of the elements of the transducer 106, and a receive circuit 116 that receives echoes received by the transducer 106. The receive circuit 116 may also be configured to process received echoes, including, beamforming (e.g., delaying and summing), spatially compounding, filtering (e.g., FIR and/or IIR), etc. the echoes.

A controller 118 controls the transmit circuit 114. Such control may include actuating or exciting individual or groups of transducer elements of the transducer 106 for an A-mode, B-mode, C-plane, etc. acquisition, steering and/or focusing the transmitted signal, etc. The controller 118 also controls the receive circuit 116. Such control may include actuating the transducer 106 for steering and/or focusing the received echoes. The controller 118 may include one or more processors that execute one or more computer readable instructions encoded or embedded in computer readable storage medium such as physical memory. Additional or alternatively, the instructions can be carried in a signal or carrier wave.

A motor controller 110 controls the motor 108, for example, to rotate the transducer array 106 based on the signal from the position sensor and a default or user selected mode of operation, which may indicate a default or user selected start angle. With reference to a 360° or greater acquisition, the start angle can be set so that the join of data 360° apart does not fall over an imaged region of interest. The motor controller 110 also controls that speed at which the transducer array 106 rotates.

A scan converter 120 scan converts the data from the receive circuit 116 to generate data for display, for example, by converting the data to the coordinate system of a display used to visually present the acquired data. The illustrated embodiment includes a display 122. However, the display 122 may alternatively be a remote device interface with the console 104.

A user interface 124 includes various input and/or output devices for interacting with the controller 118 such as buttons, knobs, a keypad, a touch screen, etc. and/or visual and/or audible output devices. The user interface 124 allows a user to activate the probe 102 and/or data acquisition via selecting a mode of operation, including an acquisition angle and/or start position.

A console communications interface 126 includes input and output ports for communicating data and control signals with the probe 102.

A communications channel $128_1$ is connected to interfaces 130 and 132 respectively for interfacing with the probe communications interface 112 and the console communications interface 126 and establishing a communications link between the probe 102 and the console 104. A communications channel $128_2$ is connected to the interface 130 and an interface 134 respectively for interfacing with the probe communications interface 112 and the motor controller 110 and establishing a communications link between the motor 108 and the motor controller 110. The channels $128_1$ and $128_2$ are collectively referred to herein as communication channel 128. The communications channel 128 may include a cable, a wire, or the like.

The illustrated communications channel 128 is shown as a separate component from the probe 102 and the console 104. However, the communications channel 128 could be part of the probe 102 in that the connections between the probe 102 and channel 128 could be fixed, whereas the connection between channel 128 and the console is open so the channel 128 can connected to the console 104 for use with the console 104 and separated therefrom when using a different probe with or not using the console 104.

It is to be appreciated that the relative geometry (e.g., size, shape, orientation, etc.) of the illustrated probe 102, console 104, and communication channel 128 are for explanatory purposes and not limiting.

Furthermore, the imaging system 100 may be configured as a hand-held unit in which an operator can readily carry the system 100 around and use the system with one or two hands, a generally portable system disposed on a cart or other device which can be used to move the system or pick up therefrom and move, or a generally stationary system affixed or residing on a surface such as the floor, a table, etc.

Figure 2:
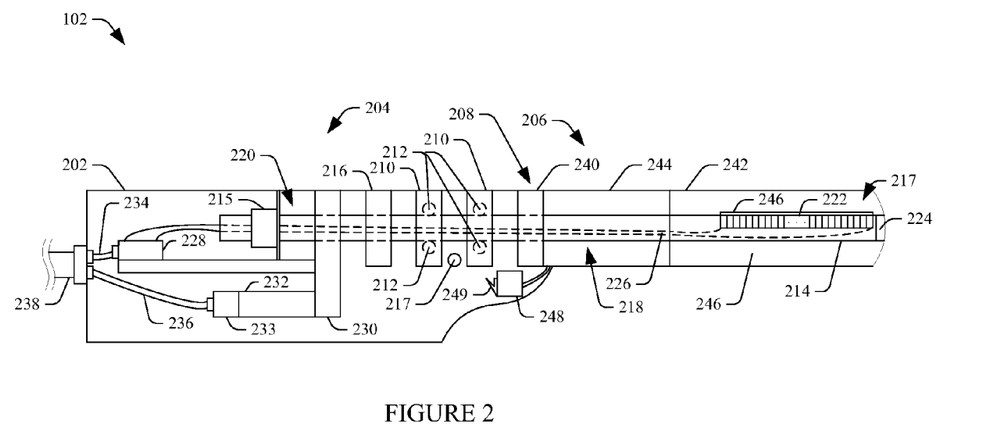
FIG. 2 illustrates an example US probe of the US imaging system.

FIG. 2 illustrates an example of the probe 102.

The illustrated probe 102 includes a housing 202 having a long axis, and a first or carrying region 204 configured to be held in a human hand, a second or tubular elongate region 206 shaped to fit a cavity such as the rectal or vaginal cavity of a human or animal subject, and a third or intermediary region 208 between and connecting the first region 204 and the second region 206. The intermediary region 208 may include a relatively more rigid material such a metal, plastic, etc. than the regions 204 and 206.

Inside the housing 202, at least one set of mechanical bearings 210 is stationarily affixed to the intermediary region 208. The illustrated bearings 210 include casings and one or more non-electrically conductive members 212 configured to allow rotational motion. Such members 212 electrically isolate the transducer array 222 from the electronics used to rotate the transducer array 222, which may mitigate electrical noise therefrom. An example of a suitable non-conductive member 212 includes, but is not limited to, a ceramic or other non-electrically conductive ball, roller, or the like. In another example, the one or more non-electrically conductive members 212 include a non-electrically conductive fluid such as a gas, a liquid, or the like.

A rotation limiting device 216 is affixed to the intermediary region 208 adjacent to the bearings 210. The rotation limiting device 216 is configured to allow a tubular structure inserted into the bearings 210 to rotate through a pre-determined angular range. As described in greater detail below, in the illustrated embodiment, the rotation limiting device 216 also such a structure rotate over five hundred and sixty degrees (560°), and the rotation limiting device 216 includes a home position and at least one member that limits rotation therefrom.

A shaft or tubular transducer array carrier 214 having an internal material free cavity is rotatably supported by the bearings 210, which allow the carrier 214 to rotate in either direction, and extends through the rotation limiting device 216. The tubular transducer array carrier 214 includes a first end portion 218 that extends into the elongate region 206 and a second end portion 220 that extends into the first region 204. A bearing 224 rotatably supports the end of the elongate region 206.

The first end portion 218 of the shaft 214 carries a transducer array 222. As discussed herein, the transducer array 222 may include a linear array of 192 transducer elements or other configuration of transducer elements. Generally, the tubular transducer array carrier 214 extends into the elongate region 206 near to the end of the region 206, and the transducer array 222 is positioned adjacent near the end of the first end portion 218. This minimizes the amount of the second region 206 of the probe 102 inserted into a subject that is beyond the area that can be seen in the live image.

An electrical pathway 226 is affixed to and in electrical communication with the transducer elements of the transducer array 222 and extends from the transducer array 222, through the tubular transducer array carrier 214 and the second end portion 220, and out the second end portion 220 where the electrical pathway 226 is affixed to an electrical connector 228, which is affixed to a support member in the first region 204.

In the illustrated embodiment, the electrical pathway 226 includes a flexible coaxial bundle of electrically conductive members such as wires, fibers, etc. In one instance, the bundle includes a separate wire for each transducer element. In another instance, the bundle includes less wires and a multiplexor or the like is utilized for transfer control signals to and/from the elements.

The flexible coaxial bundle is configured to twist through the predetermined angular range of the tubular transducer array carrier 214. The total twist is limited by end stop mechanism 216, for example, to prevent the possibility of damaging the coaxial bundle. In one instance, this includes being in an untwisted state at one extent of the rotational motion (e.g., zero or 560° degrees) and in a twisted state at the other extent of the rotational motion (e.g., 560° or zero degrees). In another instance, the flexible bundle is in the untwisted state at an angle between the two angular extents. In the former case, the flexible bundle twists and untwists in only one direction. In the latter case, the flexible bundle twists and untwists in two rotationally opposing directions. In one instance the bundle consists of one micro-coaxial (e.g., a 40AWG or smaller coaxial wire) wire for each of the rotating array elements. In another instance, the bundle may consist of one wire for more than one element of the array. In another instance the bundle consists of some number of twisted pair or twinax wires conveying analog or digital data from the rotating array to the fixed system cable.

A tube drive 230 rotates the tubular transducer array carrier 214. In the illustrated embodiment, the tubular transducer array carrier 214 includes teeth or a gear and the tube drive 230 is a toothed belt, with teeth complementary to those of the tubular transducer array carrier 214, and a motor 232 turns the belt which in turn turns the tubular transducer array carrier 214.

An index reference device 215 provides a default location of the tubular transducer array carrier 214 and hence the transducer array 222 on startup or activation of the probe 102 (i.e., turning the probe on) to position the array 222 in a known reference position. In one instance, a known reference position ensures that the image plain is aligned with a fine needle biopsy guide that can be attached and is located by a reference stud 217 inserted into the side of intermediary region 208.

A positioning device such as an encoder 233 or the like is used to track the angular or rotational position of the motor axle and hence the tubular transducer array carrier 214. In other embodiment, a toothless belt may be employed. In yet another embodiment, the motor 232 turns a gear which engages the teeth of the tubular transducer array carrier 214. Other drive devices such as a lead screw, rack and pinion, etc. are also contemplated herein.

Electrical pathways 234 and 236 interface with an electrical outlet or cable 238, which is configured to connect with the console communications port 126 (FIG. 1) of the console 104. The electrical pathways 234 and 236 provide pathways for communicating control and/or data between the probe 102 and the console 104.

The second region 206 includes an acoustic window section 242 and a support section 244, and a seal 240. The acoustic window section 242 facilitates transmission and reception of acoustic signal and echoes. The support section 244 provides structural support. The seal 240 provides a rotating seal for the fluid filled the second region 206, and is affixed in the middle portion 208 and is configured to allow rotation of the tubular transducer array carrier 214 through the predetermined rotational angle allowed by the stop device 216.

A lens 246 having a curvature matching the acoustic window portion 242 is affixed to the transducer array 222.

A coupling fluid is disposed inside the second region 206 and surrounds the tubular transducer array carrier 214, the lens 246, and the transducer array 222. The coupling fluid acoustically couples the transducer elements of the transducer array 222 and the acoustic window portion 242.

A fluid reservoir 248 allows for expansion and contraction of the coupling fluid (e.g., due to temperature changes, pressure changes, etc.) by providing a deformable (expandable and collapsible) chamber into which the coupling fluid can flow between the below and the second region 206. The fluid reservoir 248 allows for expansion and contraction of the coupling fluid, for example, as a consequence of temperature changes of the coupling fluid, and also provides replacement fluid due to fluid lost via leakage at seal 240. The fluid reservoir 248 has a spring device 249 that provides a slight positive pressure to the fluid within the second region 206 to ensure that air is kept out of the fluid.

The illustrated probe 102 is configured for imaging from inside of a cavity such as rectal and/or vaginal cavities. Depending on the particular application, the diameter of the second region 206 may differ.

Figure 3:
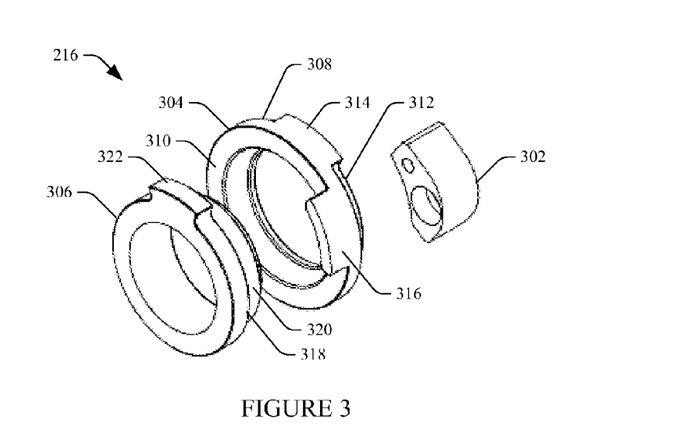
FIGS. 3 and 4 illustrate a rotation limiting device of the US probe.

FIG. 3 illustrates an example of the rotation limiting device 216.

In this example, the rotation limiting device 216 includes three elements, a stationary element 302, a first or intermediary rotating element 304, and a second or outer rotating element 306.

The stationary element 302 has a generally arc shape, and, in the illustrated embodiment, spans a predetermined relatively short segment of a circumference of a circle.

The intermediary rotating element 304 is made of an insulating plastic material to both provide electrical isolation between the rotating tube and the support housing and to absorb impact shocks when the mechanism hits the end stops. Absorbing the shocks here may reduce the wear on the drive system. The intermediary rotating element 304 includes a generally annular ring and includes first and second faces 308 and 310 on opposing sides.

The first face 308 includes a recess 312 that runs along a substantial portion of a circular path on the first face 308. The first face 308 also includes a first protrusion 314 having a generally arc shape and that protrudes generally perpendicularly out of the first face 308 from the circular path such that the recess 312 runs only from one side of the protrusion 314 along the circular path to the other side of the protrusion 314. The second face 310 is generally planar and includes a second protrusion 316 having a generally arc shape and that protrudes generally perpendicularly out of the second face 310 from the circular path.

The first and second protrusions 314 and 316 protrude in opposing directions away from intermediary rotating element 304. In the illustrated embodiment, the first and second protrusions 314 and 316 are offset from each other along a transverse direction, which is generally parallel to a plane along the diameter of the intermediary rotating element 304. In other embodiment, the first and second protrusions 314 and 316 can be otherwise offset or protrude from a similar location along the annular ring of the intermediary rotating element 304.

The outer rotating element 306 includes a generally annular ring and has a face 318. The face 318 includes a recess 320 that runs along a circular path on the first face 308. The face 318 also includes a protrusion 322 having a generally arc shape and that protrudes generally radially from the annular ring.

Figure 4:
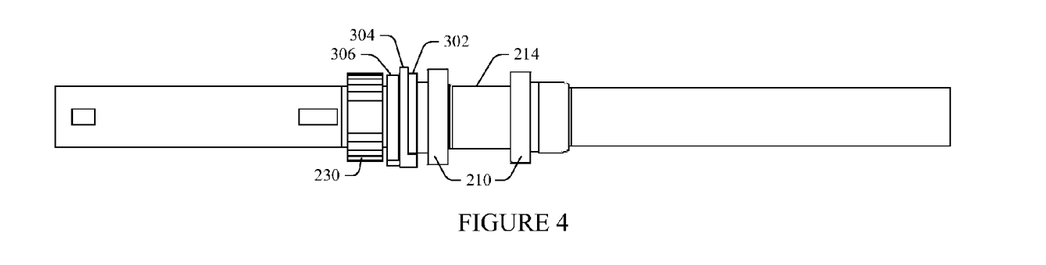

FIG. 4 shows the example rotation limiting device 216 of FIG. 3 in connection with a portion of the probe 102 of FIG. 2. From FIG. 2, the probe 102 includes the bearings 210, which rotatably support the tubular transducer array carrier 214, and the tube drive 230, which rotates the tubular transducer array carrier 214.

The stationary portion 302 is fixedly mounted to the intermediary region 208 (FIG. 2) of the housing 202 (FIG. 2). The intermediary rotating element 304 is rotatably couples to the stationary portion 302. For example, in the illustrated embodiment the arc of the stationary element 302 follows a circle that matches (e.g., has the same diameter as) the circular path of the intermediary rotating element 304 followed by the recess 312 of the intermediary rotating element 304.

As such, the elements 302 and 304 are coupled so that the stationary element 302 sits in the recess 312 of the intermediary rotating element 304. With such a coupling, the intermediary rotating element 304 can rotate, relative to the stationary element 302, through an angular range from where one side of first protrusion 314 physically contacts the stationary element 302 in the recess 312 to where the other side of the first protrusion 314 physically contacts the other side of stationary element 302 in the recess 312.

The outer rotating element 306 is affixed to the tubular transducer array carrier 214 and is rotatably coupled to the intermediary rotating element 304. For example, in the illustrated embodiment the recess 320 of the outer rotating element 306 sits in and follows an aperture of the intermediary rotating element 304, with the face 318 of the outer rotating element 306 facing the planar surface of the second face 310 of the intermediary rotating element 304.

With this coupling, the outer rotating element 306 can be rotated, relative to the intermediary rotating element 304, through an angular range from where one side of protrusion 322 of the outer rotating element 306 physically contacts the second protrusion 316 of the intermediary rotating element 304 to where the other side of the protrusion 322 of the outer rotating element 306 physically contacts the other side of the second protrusion 316 of the intermediary rotating element 304.

The angular range of the intermediary rotating element 304 will depend on the physical lengths of the arcs of stationary element 302 and the protrusion 314, and the angular range of the outer rotating element 306 will depend on the physical lengths of the arcs of the protrusion 322 of the outer rotating element 306 and the protrusion 316 of the intermediary rotating element 304. The combination of the two angular ranges defines the angular range of rotation for the tubular transducer array carrier 214.

By way of example, where the intermediary rotating element 304 is configured to rotate two hundred and eighty degrees (280°) and the outer rotating element 306 is configured to rotate two hundred and eighty degrees (280°), the tubular transducer array carrier 214 can be rotated five hundred and sixty degrees (560°) (or 280°±280°). Of course, the angular rotation of the intermediary rotating element 304 and the outer rotating element 306 does not have to be equal as in the above example. This total angle can also be changed as required to accommodate manufacturing tolerances to ensure that the rotation of the array meets its minimum total angle.

Figure 5:
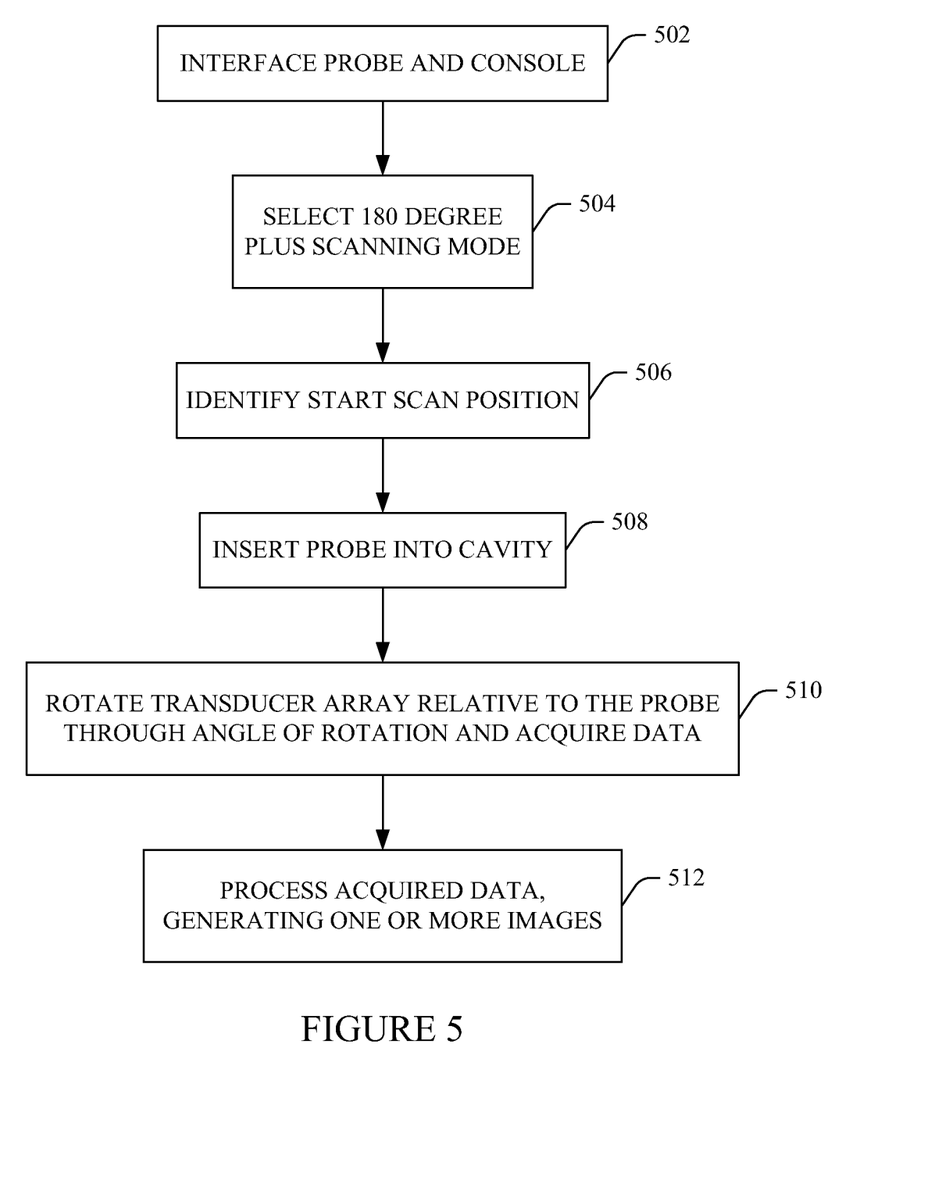
FIG. 5 illustrates an example method.

FIG. 5 illustrates a method for imaging with the system 100.

Note that the ordering of the following acts is for explanatory purposes and is not limiting. As such, one or more of the acts can be performed in a different order, including, but not limited to, concurrently. Furthermore, one or more of the acts may be omitted and/or one or more other acts may be added.

At 502, the probe 102 is electrically connected to the console 104. As described herein, this includes interfacing the probe 102 and console 104 via respective communication ports 112 and 126 and the communications channel 128.

At 504, a scanning mode is selected. As described herein, this may be achieved by the controller 118 receiving a signal from the user interface 124 wherein the signal is indicative of a user selected mode of interest. The scanning mode may be for a 3D data acquisition covering an angular range greater than one hundred and eighty degrees. Mode with angular ranges of less than one hundred and eighty degrees can alternatively be selected.

At 506, a start scan position is identified, and the transducer array 222 is positioned accordingly. As described herein, the start position may be a default or a user selected start position. For the latter case, the use can employ controls of the user interface 124 to specify a scan start position of interest. An example of a user selected start scan position is provided below in connection with FIGS. 6 and 7.

The user interface 124 may include one or more controls for rotating the transducer array in either direction (within the limits of rotation) in predetermined angular increments such as, for example, one to two degrees or other number of degrees per increment. In another embodiment, the transducer array is configured to continuously move while a control is actuated.

At 508, the probe 102 is inserted into the cavity which the imaging procedure will take place. For example, where the probe 102 is a trans-rectal probe, the probe 102 is inserted into the rectal cavity of the patient being scanned, where the probe 102 is a trans-vaginal probe, the probe 102 is inserted into the vaginal cavity of the patient being scanned, etc.

At 510, the transducer array is rotated through the angular range for the scan and ultrasound data is acquired. Where the acquisition covers an angular range of greater than on hundred and eighty degrees, this includes rotating the transducer array more than one hundred and eighty degrees.

At 512, the acquired data is processed and one or more images of the internal structure of the patient are generated.

Figure 6:
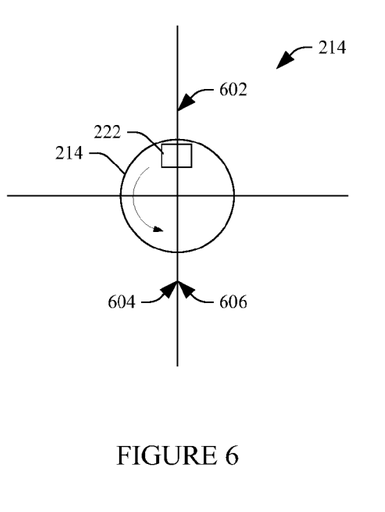
FIGS. 6 and 7 provide a non-limiting example in which a user defines a start scan position of the US probe that is different from the default start scan position.
Figure 7:
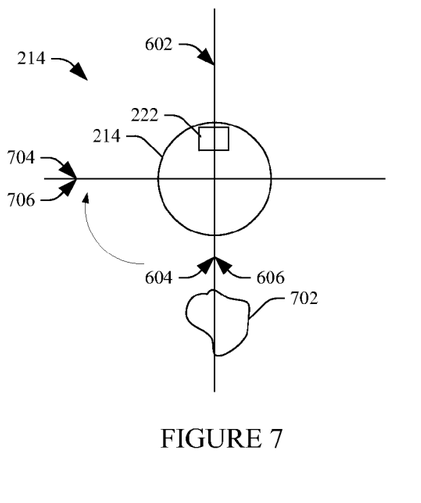

FIGS. 6 and 7 provide a cross-sectional view of the shaft 214 in connection with a non-limiting example in which a user defines a start scan position.

Initially referring to FIG. 6, in this example, a home rotational position 602 of the shaft 214 aligns the transducer array 222 so that it is facing up in this example. A default scan start rotational position 604 is located one hundred and eighty degrees from the home rotational position 602, facing down in this example, and is also the end scan rotational position 606 for a 360 degree scan.

In the illustrated embodiment, the shaft 214 rotates counter-clockwise to move the transducer array 222 from the home rotational position 602 to the default start scan rotational position 604. During a 360 degree scan, the shafts 214 rotates the transducer array 222 360 degrees from the default start scan rotational position 604 to the end scan rotational position 606.

In other embodiments, the home rotational position 602 and/or the default start and end scan rotational positions 604 and 606 can be otherwise located, and the shaft 214 may rotate clockwise to move the transducer array 222 from the home rotational position 602 to the default start scan rotational position 604.

Turning to FIG. 7, anatomy of interest 702 is located relative to the shaft 214 such that the default scan start and end rotational positions 604 and 606 for a 360 degree scan falls within the anatomy of interest 702, which may introduce artifact in the image of the anatomy of interest 702.

In this example, the user has changed the start scan rotational position from the default start scan rotational position 604 to an alternative start scan rotational position 704 and, hence, also changed the end scan rotational position 606 for a 360 degree scan to an alternative end scan rotational position 706. At this location, neither the start scan rotational position 704 nor the end scan rotational position 706 for a 360 degree scan fall within the anatomy of interest 702, mitigating introducing artifact in the image of the anatomy of interest 702 due to the start and end rotational positions falling within the anatomy of interest 702.

In the illustrate example, the alternative start scan rotational position 704 is rotationally shifted 90 degrees clockwise (+90) from the default start scan rotational position 604. In another embodiment, the alternative start scan rotational position 704 can be rotationally shifted 90 degrees counter-clockwise (−90) from the default start scan rotational position 604. In yet another embodiment, the magnitude of the rotational shift from the default start scan position 604 may be greater or less than 90 degrees.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging probe, comprising:
   a housing having a long axis;
   an elongate tubular shaft entirely located in the housing and including an internal cavity and first and second end portions, wherein the shaft extends along the long axis and is rotatably supported in the housing for rotation relative to the entirety of the housing through an angular range including one hundred and eighty degrees to a predetermined maximum angle, which is greater than one hundred and eighty degrees;
   a rotation limiting device entirely located and affixed in the housing, wherein the rotation limiting device allows the shaft to rotate up to only the predetermined maximum angle relative to the housing, wherein the rotation limiting device comprises:
      a stationary element stationarily affixed in the housing;
      rotating element rotatably coupled to the stationary element to rotate over a first predetermined angular range; and
      a second rotating element affixed to the shaft and rotatably coupled to the first rotating element to rotate over a second predetermined angular range, wherein the first and second angular ranges combine to provide the predetermined maximum angle;
   a transducer array, including a plurality of transducer elements along the long axis, affixed to the first end portion of the shaft;
   an electrical connector fixedly mounted in the housing; and
   an physical electrical pathway having first and second ends and extending along and in the internal cavity of the shaft, wherein a first end of the pathway is connected to transducer array and a second end of the pathway is connected to the electrical connector.

2. The probe of claim 1, further comprising: a tube drive entirely located in the housing and configured to rotate the elongate tubular shaft.

3. The probe of claim 2, wherein the elongate tubular shaft includes teeth, and wherein the tube drive includes a toothed belt with teeth complementary to those of the elongate tubular shaft, and further comprising:
   a motor configured to turn the toothed belt which in turn turns the elongate tubular shaft.

4. The probe of claim 2, wherein the stationary portion extends along an arc segment, and wherein the first rotating element comprises:
   an annular ring with a first face;
   a recess extending along a portion of a circular path along the first face; and
   a protrusion extending out of the circular path;
   wherein the stationary element sits in the recess and the first rotating element rotates about the stationary element from a first position in which the protrusion physically contacts a first end of the stationary element to a second position in which the protrusion physically contacts a second end of the stationary element.

5. The probe of claim 2, wherein the first rotating element comprises:
   first annular ring with a first face;
   a generally planar face; and
   a first protrusion extending out of the first face; and
   wherein the second rotating element comprises:
   a second annular ring with a second face;
   a recess extending along a portion of a circular path along the second face; and
   a second protrusion extending out of the circular path, wherein the second protrusion extends perpendicular to the first protrusion;
   wherein the recess of the second rotating element sits in an aperture of the second annular ring, and the second rotating element rotates about the first rotating element from a first position in which the second protrusion physically contacts a first end of the first protrusion through intermediate positions in which the second protrusion does not physically contact the first protrusion to a second position in which the second protrusion physically contacts a second opposing end of the first protrusion.

6. The probe of claim 1, wherein the maximum angle is five hundred and sixty degrees or more.

7. The probe of claim 1, further comprising:
   at least one bearing affixed in the housing, wherein the bearing rotatably supports the shaft for rotation over the angular range.

8. The probe of claim 7, wherein the bearing comprises:
   a non-electrically conductive member which supports the shaft for rotation over the angular range.

9. The probe of claim 8, wherein the non-electrically conductive member comprising at least one ceramic ball.

10. The probe of claim 1, wherein the electrical pathway includes a bundle of electrical conductive wires, and the first end of the electrical pathway rotates with the transducer array and the second end remains stationary with the electrical connector.

11. The probe of claim 10, wherein the electrical pathway is configured so that the electrical pathway is in an untwisted state at one end of the angular range and in a twisted state at the other end of the angular range.

12. The probe of claim 1, wherein the housing comprises:
a tubular elongate region shaped for insertion into a cavity of interest for imaging from inside the cavity, wherein the first end portion of the shaft carrying the transducer array extends in the tubular elongate region, and wherein the tubular elongate region is filled with an acoustic coupling fluid; and
a seal that surrounds and seals the tubular elongate portion.

13. The probe of claim 12, further comprising:
a fluid reservoir that extends a volume of the sealed tubular elongate region that at least one of holds expanding coupling fluid that can no longer fit into the sealed tubular elongate region, provides a source of coupling fluid to ensure the sealed tubular elongate region is filled with coupling fluid, and includes a spring device that applies a pressure to inhibit air from entering the sealed tubular elongate region.

14. The probe of claim 1, wherein the probe is at least one of a trans-rectal or a trans-vaginal probe.

15. The probe of claim 1, wherein the stationary element has an arc shape that spans a predetermined segment of a circumference of a circle.

16. The probe of claim 15, wherein the first rotating element comprises: a first annular ring, which includes: a first face with a first recess that runs along a portion of a first circular path on the first face and with a first protrusion having an arc shape and that protrudes perpendicularly out of the first face from the first circular path such that the first recess runs only from one side of the first protrusion along the first circular path to an opposing side of the first protrusion.

17. The probe of claim 16, wherein the first rotating element further comprises: a second face on side opposing the first face, wherein the second face is planar and includes a second protrusion having an arc shape and that protrudes perpendicularly out of the second face from the first circular path.

18. The probe of claim 17, wherein the first and second protrusions protrude in opposing directions away from the first annular ring.

19. The probe of claim 18, wherein the first and second protrusions are offset from each other along a transverse direction, which is parallel to a plane along a diameter of the second rotating element.

20. The probe of claim 18, wherein the second rotating element comprises: a second annular ring, including: a third face with a second recess that runs along a second circular path on the third face and with a third protrusion having an arc shape and that protrudes radially from the second annular ring.

21. The probe of claim 20, wherein the arc shape of the stationary element is configured to follows a circle with a same diameter as the first circular path of the first rotating element.

22. The probe of claim 21, wherein the stationary element sits in the first recess of the first rotating element.

23. The probe of claim 22, wherein the second recess sits in and is configured to follow an aperture of the first rotating element, with the third face of the second rotating element facing the planar second face of the first rotating element.

* * * * *